United States Patent [19]

Vignaud et al.

[11] Patent Number: 5,129,388
[45] Date of Patent: Jul. 14, 1992

[54] DEVICE FOR SUPPORTING THE SPINAL COLUMN

[76] Inventors: Jean-Louis Vignaud, 10 impasse F. Audouin, F-33400 Talence; Jean-Francois Sacriste, 5 Square Maurice Ravel, 33115 Le Pyla sur Mer; Gilles Missenard, 94-96 quai Louis Blériot, F-75016 Paris; Philippe Lapresle, 32 boulevard Victor Hugo, F-92200 Neuilly sur Seine, all of France

[21] Appl. No.: 582,901

[22] PCT Filed: Feb. 8, 1990

[86] PCT No.: PCT/FR90/00096
§ 371 Date: Oct. 9, 1990
§ 102(e) Date: Oct. 9, 1990

[87] PCT Pub. No.: WO90/09156
PCT Pub. Date: Aug. 23, 1990

[30] Foreign Application Priority Data

Feb. 9, 1989 [FR] France .................. 89 01923

[51] Int. Cl.$^5$ ............................................. A61F 5/00
[52] U.S. Cl. ...................................... 606/61; 411/385; 411/393
[58] Field of Search .............. 128/69; 606/60-62, 606/72; 411/385; 403/347, 362

[56] References Cited

U.S. PATENT DOCUMENTS

| | | | |
|---|---|---|---|
| 4,743,260 | 5/1988 | Burton | 623/17 |
| 4,763,644 | 8/1988 | Webb | 128/69 |
| 4,815,453 | 3/1989 | Cotrel | 128/69 |
| 4,913,134 | 4/1990 | Luque | 128/69 |
| 4,946,458 | 8/1990 | Harms et al. | 606/61 |
| 4,950,269 | 8/1990 | Gaines, Jr. | 128/69 |

FOREIGN PATENT DOCUMENTS

| | | | |
|---|---|---|---|
| 0128058 | 12/1984 | European Pat. Off. | |
| 0283373 | 9/1988 | European Pat. Off. | |
| 0348272 | 12/1989 | European Pat. Off. | |
| 3722590 | 12/1988 | Fed. Rep. of Germany | 606/61 |
| 2506605 | 12/1982 | France | |
| 2559378 | 8/1985 | France | |
| 2624720 | 6/1989 | France | |
| 780652 | 8/1957 | United Kingdom | 128/69 |
| 2173104A | 10/1986 | United Kingdom | |

Primary Examiner—Richard J. Apley
Assistant Examiner—Susan L. Weinhoffer
Attorney, Agent, or Firm—Roylance, Abrams, Berdo & Goodman

[57] ABSTRACT

A device for supporting a spinal column includes a screw having a U-shaped head, a joining element received within the head, a threaded bolt received within and threadedly engaging the head, and a cap covering an upper portion of the head. The head is internally threaded. The threaded bolt engages the joining element to block relative movement between the joining element and the screw. The cap avoids spreading of the head upon tightening of the bolt in the head.

13 Claims, 4 Drawing Sheets

DEVICE FOR SUPPORTING THE SPINAL COLUMN

FIELD OF THE INVENTION

The present invention relates to a device to contain, reduce and re-establish physiological curves to the spine of a patient by implanting a diapason screw spinal instrument. The screws have U-shaped heads for receiving on element integrally connecting the various screws with one another.

BACKGROUND OF THE INVENTION

Normally, pedicular screws joined by plates are implanted. However, this implantation depended on the spatial requirement of the holes of the plates, hence requiring a correct setting but small reduction.

Hooks are also implanted laid on the posterior arches moving around on rods with complex blocking systems. These systems allow for a correct setting and reduction but firstly require observance of the posterior vertebral arches and secondly delicate to-and-fro manoeuvres, dangerous for the patient and scarcely practical for the operator.

SUMMARY OF THE INVENTION

The device of the invention makes it possible to overcome all these drawbacks. In effect, it comprises several screws composed of three segments: particular head/-body point, a bolt, a cap and a homolateral joining element.

The structure and adaptation of this equipment has been specially created to this effect.

The screw is made of homologous materials for use in surgery so as to avoid the equipment breaking when it penetrates into the vertebral body.

The point of the screw has an inverted pyramidal square shape. The body of the screw is conical and bears a standard cortical thread which allows for improved blocking of the implant in the most fragile region of the vertebral pedicule.

Moreover, this conicity reinforces the solidity of the body of the screw at the screw head.

The head of the screw has a a U-diapason shape for receiving the element for rendering the various screws integral with one another. The bottom of the U is slightly rounded so as to enable the joining element to be fixed in several positions, which also facilitates the blocking of the joining element.

The U is threaded at the internal section of the branches so as to allow for screwing in situ of a bolt locking the joining element. As the risk of this system concerns the spatial requirement of the branches of the U at the time of screwing, this risk can be avoided by placing a cap able to fit exactly on the outer smooth section of the branches of the U. This cap comprises a circular orifice to allow for the tightening and definitive blocking of the bolt blocking the joining rod.

The bolt is characterized by a threaded cylindrical shape bearing at its extremity a male conical point able to be fit perfectly into the female conical notches of the joining rod. The opposing section of the bolt comprises a hexagon-shaped cavity enabling it to receive a chuck key.

The joining element is made of a homologous material for surgical implantation. This is a rod with a cylindrical section and having a sufficient diameter so as to resist the stresses and forces of the spine, said rod being notched to allow for a micrometric adjustment of the various screws in relation to one another. Each notch has a female conical shape so as to receive the point of the bolt. Depending on the adjustment to be obtained, the notching shall have one variable pitch.

The diameter of the joining element is sufficient so to render it resistant whilst allowing for easy shaping so as to be adapted to or re-establish the physiological curves of the spine. In addition, its circular section enable it to be rotated prior to being locked, this being effected after a correct positioning of the joining element by tightening the bolt of the various homolateral screws.

This rod is easily placed owing to the adaptation of the head screws as it may be positioned directly at the bottom of the U without requiring any forced movement or the need for any to-and-fro sliding.

The structure in itself of the diapason implant, by modifying the size of the screw or by adapting the screw head to other osteosynthesis posterior arch systems, makes it possible to make vertebral fixings over the entire height of the spine, regardless of the level and type of instrumented vertebra by retaining the same joining element.

BRIEF DESCRIPTION OF THE DRAWINGS

FIG. 2b is a sectional view of the screw of FIG. 2a.

FIG. 5b is a sectional view of the cap as shown in FIG. 5a.

DESCRIPTION OF THE PREFERRED EMBODIMENT

Figure 1:
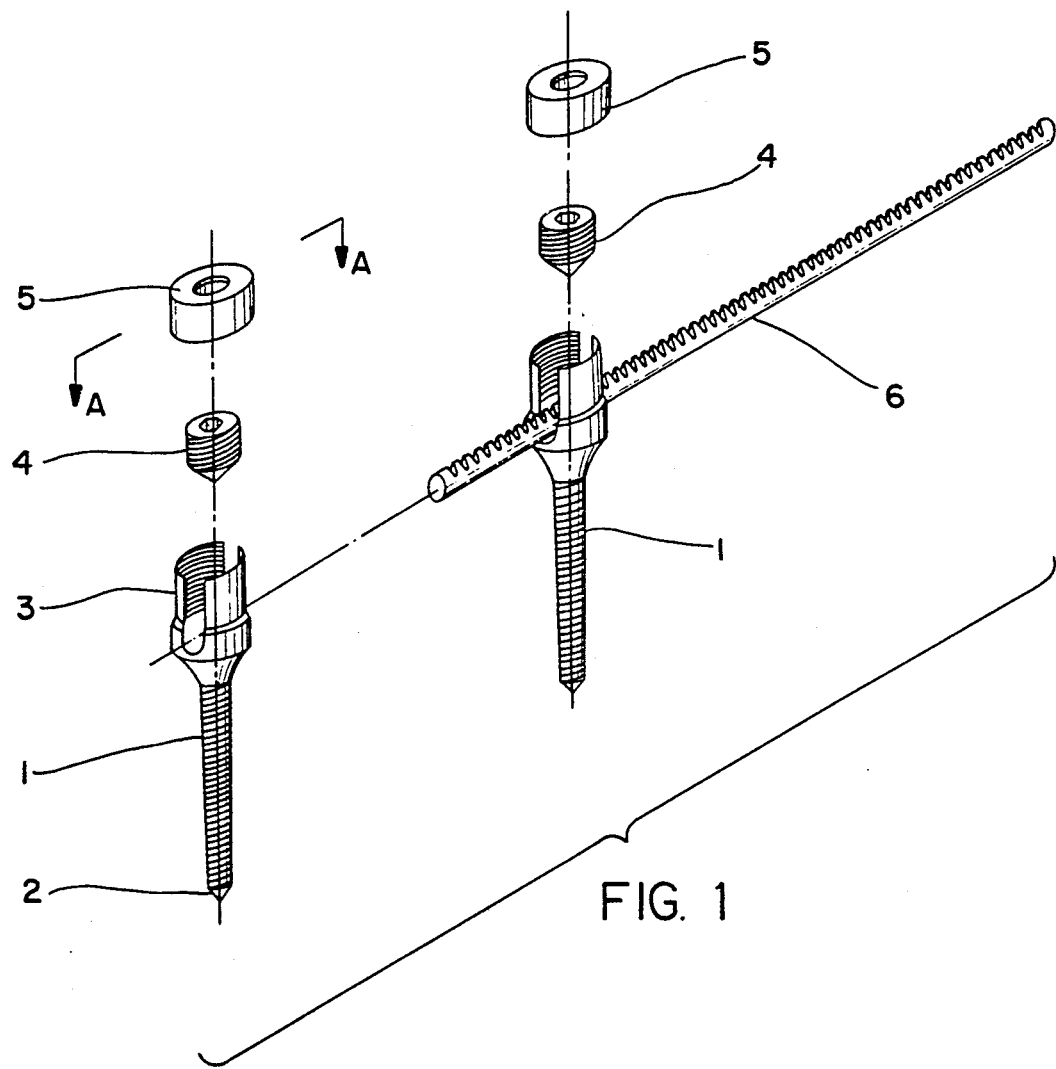
FIG. 1 is a view of two screws and their connecting element.

The device shown on FIG. 1 comprises two conical screws (1) with a point (2), a body (1), a U-shaped diapason (3), a bolt (4), a cap (5) and a joining element (6).

Figure 2A:
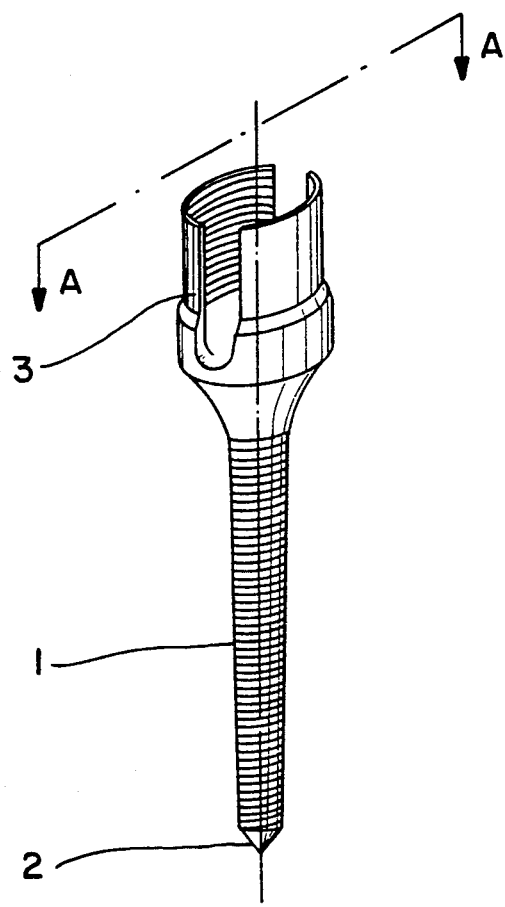
FIG. 2a is a view of a cortical conical screw.
Figure 2B:
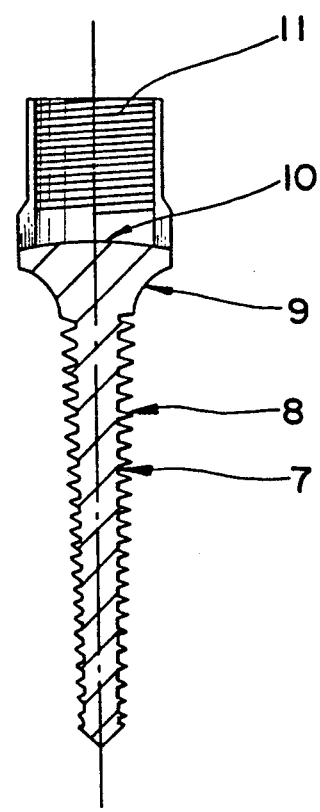

The device shown on FIGS. 2a and 2b comprises a standard cortical conical screw (1) with a square point (2) at its lower extremity.

The body of the screw (1) exhibits double conicity: namely, conicity of the core of the screw (7) differing from that of the top of the thread (8).

The U-shaped diapason head (3) is connected to the body of the screw by a radius (9) reinforcing the solidity of the body of the screw at its point for joining with the vertebral pedicule. The bottom of the U is slightly rounded (10) so as to allow for a multi-axial blocking of the joining element (6). The upper diameter of the U (3) is smaller at its upper section than at its lower section. By means of sliding adjustment, this makes it possible to receive the cap (5).

The internal section of the U is threaded (11) and receives a bolt (4) enabling the joining element to be blocked.

Figure 3:
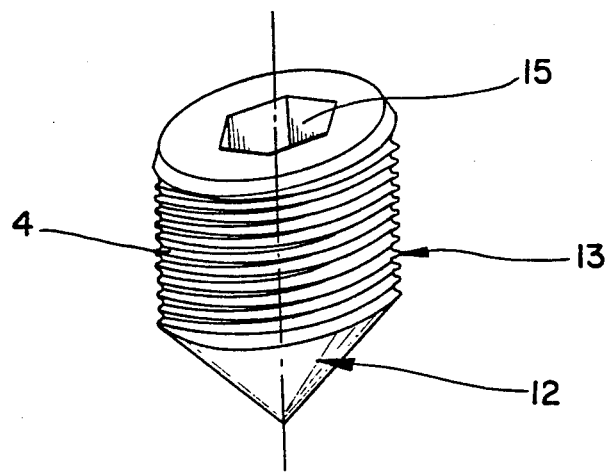
FIG. 3 is a view of the bolt used in the U-shaped diapason.

The device shown on FIG. 3 comprises a bolt (4) with a conical section (12) at its lower extremity. A threaded cylindrical section (13) is screwed into the body of the U (3) by being adapted to the threads (11).

The conical section (12) is adapted to the female conical section (14) of the joining element (6).

The upper section of the bolt (4) comprises a hollow hexagonal cavity (15) able to receive a chuck key.

Figure 4:
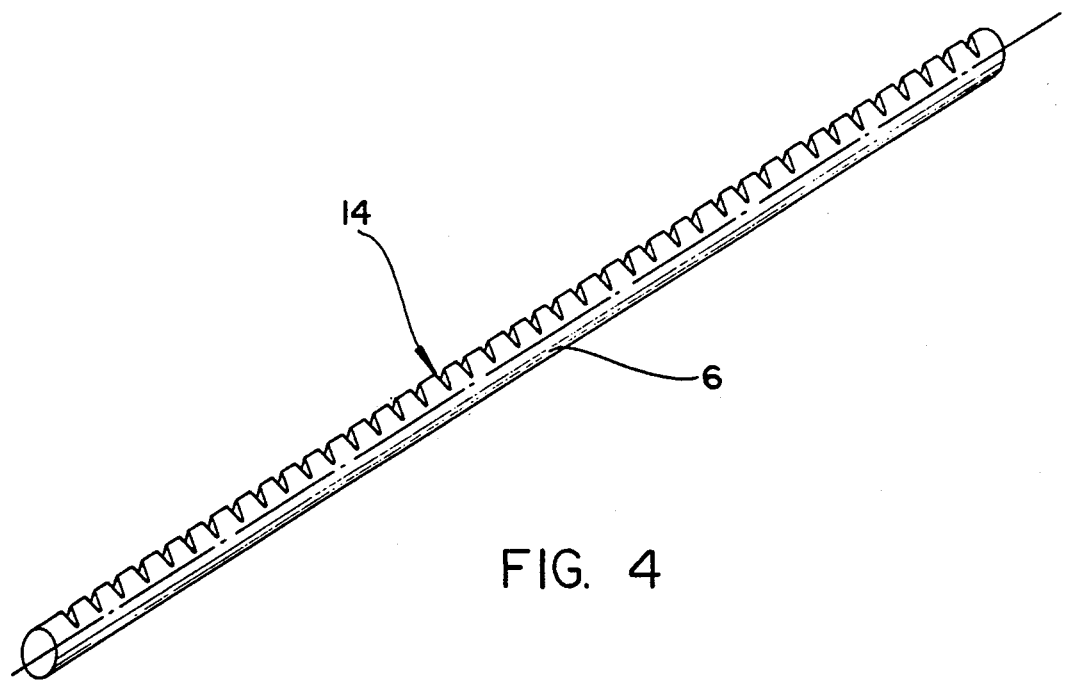
FIG. 4 is a view of the joining element.

The device shown on FIG. 4 comprises a joining element (6) for rendering integral the various screw of FIGS. 2, 3 and 4.

This joining element (6) has a cylindrical section.

Figure 5A:
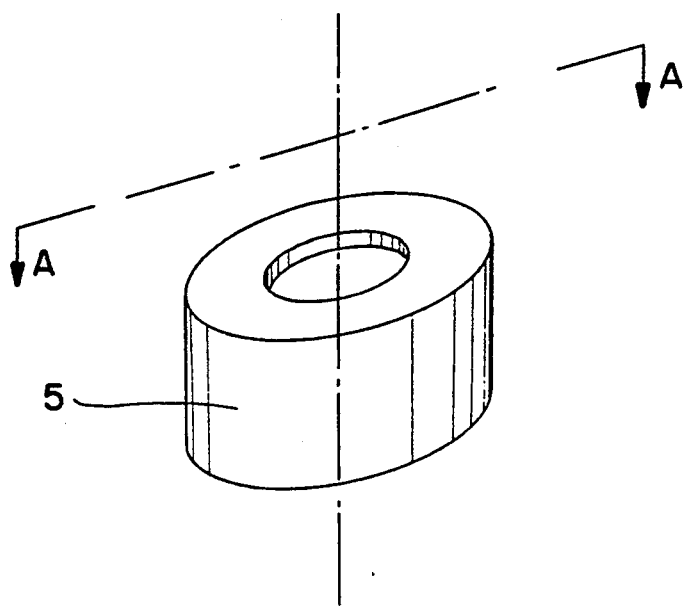
FIG. 5a is a detailed view of the cap as shown in FIG. 1.
Figure 5B:
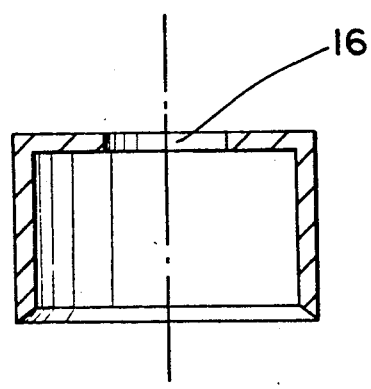

This joining element (6) is notched (14) so as to allow for the micrometric adjustment of the screws in relation to one another with the aid of the bolt (4). The female conical notches (14) receive the point (12) of the bolt (4). The device shown on FIGS. 5a and 5b comprises a cylindrical cap (5) able to be fitted by chucked sliding onto the top of the U (3). The upper section comprises an orifice (16) allowing for the passage of the chuck key of the bolt (4).

What is claimed is:

1. A device for supporting a spinal column, comprising:
    a screw having a U-shaped head, said head being internally threaded;
    a joining element received within said head;
    an externally threaded bolt received within and threadedly engaging said head, and engaging said joining element to block relative movement between said joining element and said screw; and
    a cap covering an upper outer portion of said U-shaped head to avoid spreading of said head upon tightening of said bolt in said head.

2. A device according to claim 1 wherein
said screw comprises external threads having a conicity which differs between a core of said threads and a top of said threads.

3. A device according to claim 1 wherein
said upper portion of said U-shaped head has a generally cylindrical outer surface with upper and lower sections, said upper section having a smaller transverse diameter than said lower section.

4. A device according to claim 1 wherein
said U-shaped head has an internal bottom portion which receives said joining element, said bottom portion being rounded in two planes.

5. A device according to claim 1 wherein
said screw comprises a section connecting said U-shaped head to an externally threaded portion thereof, said section being a concave-shaped quarter circle.

6. A device according to claim 1 wherein
said bolt comprises a conical base; and
said joining element comprises a series of longitudinally spaced, preformed notches, one of said notches receiving said conical base when said bolt is tightened in said U-shaped head.

7. A device according to claim 3 wherein
said cap comprises a generally cylindrical inner surface mating with said upper section of said outer surface of said U-shaped head to provide a tight sliding connection therebetween.

8. A device according to claim 7 wherein
said cap comprises a top section with a circular orifice for allowing a tool to pass through said cap and to engage said bolt.

9. A device according to claim 8 wherein
said bolt has an upper section with means for receiving and engaging the tool.

10. A device according to claim 1 wherein
said joining element comprises a rod with a cylindrical section and preformed conical notches on a periphery of said rod; and
said bolt having a base received in one of said notches.

11. A device according to claim 10 wherein
said notches are machines at various pitches for micrometric positioning adjustment of said joining element in said U-shaped head.

12. A device according to claim 1 wherein said joining element is coupled to other devices.

13. A device according to claim 1 wherein
said cap comprises a generally cylindrical, unthreaded inner surface.

* * * * *